United States Patent
Klocke et al.

(10) Patent No.: US 10,512,712 B2
(45) Date of Patent: Dec. 24, 2019

(54) POLYLACTIDE-COATED IMPLANT COMPOSED OF A BIOCORRODIBLE MAGNESIUM ALLOY

(75) Inventors: Bjoern Klocke, Zurich (CH); Alexander Borck, Aurachtal (DE)

(73) Assignee: BIOTRONIK AG, Buelach (CH)

( * ) Notice: Subject to any disclaimer, the term of this patent is extended or adjusted under 35 U.S.C. 154(b) by 859 days.

(21) Appl. No.: 13/191,647

(22) Filed: Jul. 27, 2011

(65) Prior Publication Data

US 2012/0035716 A1 Feb. 9, 2012

Related U.S. Application Data

(60) Provisional application No. 61/370,101, filed on Aug. 3, 2010.

(51) Int. Cl.
| | |
|---|---|
| *A61L 31/02* | (2006.01) |
| *A61F 2/82* | (2013.01) |
| *A61L 31/10* | (2006.01) |
| *A61L 31/14* | (2006.01) |

(52) U.S. Cl.
CPC .............. *A61L 31/022* (2013.01); *A61F 2/82* (2013.01); *A61L 31/10* (2013.01); *A61L 31/14* (2013.01); *A61L 31/148* (2013.01)

(58) Field of Classification Search
None
See application file for complete search history.

(56) References Cited

U.S. PATENT DOCUMENTS

| | | | |
|---|---|---|---|
| 2003/0068355 A1* | 4/2003 | Shanley et al. | 424/426 |
| 2004/0034409 A1* | 2/2004 | Heublein et al. | 623/1.46 |
| 2005/0187607 A1* | 8/2005 | Akhtar et al. | 623/1.15 |
| 2006/0052864 A1* | 3/2006 | Harder et al. | 623/1.38 |
| 2007/0014739 A1* | 1/2007 | Eldridge | A61Q 11/00 424/49 |
| 2007/0207186 A1* | 9/2007 | Scanlon et al. | 424/424 |
| 2009/0138077 A1* | 5/2009 | Weber et al. | 623/1.46 |
| 2009/0248147 A1* | 10/2009 | Wang | 623/1.49 |
| 2011/0034996 A1* | 2/2011 | Borck | 623/1.46 |

FOREIGN PATENT DOCUMENTS

| | | |
|---|---|---|
| EP | 1977722 A1 | 10/2008 |
| EP | 2116576 A1 | 11/2009 |
| EP | 2289575 A2 | 3/2011 |
| WO | 2008089434 A2 | 7/2008 |

* cited by examiner

*Primary Examiner* — Leslie Lopez

(74) *Attorney, Agent, or Firm* — Greer, Burns & Crain, Ltd.; Steven P. Fallon

(57) ABSTRACT

Some invention embodiments relate to an implant having a base body composed of a biocorrodible magnesium alloy and a polylactide coating. The implant is characterized in that the coating contains seed crystals and/or lipophilic substances as additives.

18 Claims, No Drawings

POLYLACTIDE-COATED IMPLANT COMPOSED OF A BIOCORRODIBLE MAGNESIUM ALLOY

CROSS REFERENCE

The present application claims priority on U.S. Provisional Application No. 61/370,101 filed on Aug. 3, 2010; which application is incorporated herein by reference.

TECHNICAL FIELD

One embodiment of the invention relates to an implant having a base body composed of a biocorrodible magnesium alloy and a polylactide coating.

BACKGROUND

Implants have found use in modern medical technology in many different embodiments. They are used, for example, for supporting vessels, hollow organs, and duct systems (endovascular implants, for example stents), for attaching and temporarily fixing tissue implants and tissue transplants, as well as for orthopedic purposes, for example as pins, plates, or screws. One form of implant used particularly often is the stent.

The implantation of stents has become established as one of the most effective therapeutic measures in the treatment of vascular diseases. Stents perform a support function in hollow organs of a patient. For this purpose, some stents have a filigreed support structure made of metallic braces, which are initially in a compressed form for insertion into the body, and are then expanded at the site of application. One of the main fields of application of such stents is to permanently or temporarily widen and keep open vascular constrictions, in particular constrictions (stenoses) of the coronary vessels. In addition, aneurysm stents, for example, are also known which are primarily used for closing off the aneurysm. The support function is also provided.

Some stents have a circumferential wall of sufficient load capacity to keep the constricted vessel open to the desired extent, and have a tubular base body through which blood flows through unhindered. The circumferential wall is generally formed by a lattice-like support structure which allows the stent to be inserted in a compressed state, with a small outer diameter, up to the constriction to be treated in the particular vessel, and at that location, for example by use of a balloon catheter, to be expanded until the vessel has the desired enlarged inner diameter. Alternatively, shape memory materials such as nitinol have the capability for self-expansion when a restoring force is discontinued, thus maintaining a small diameter of the implant. The restoring force is generally exerted on this material by a protective tube.

The implant, in particular the stent, has a base body made of an implant material. An implant material is a nonliving material which is used for medical applications and interacts with biological systems. The basic requirement for use of a material as an implant material, which when properly used is in contact with the bodily surroundings, is compatibility with the body (biocompatibility). Biocompatibility is understood to mean the ability of a material to induce an appropriate tissue reaction in a specific application. This includes adaptation of the chemical, physical, biological, and morphological surface characteristics of an implant to the recipient tissue, with the objective of a clinically sought interaction. The biocompatibility of the implant material is also dependent on the time sequence of the reaction of the biosystem which has received the implant. Relatively short-term irritation and inflammation occur which may result in changes in the tissue. Accordingly, biological systems react in various ways, depending on the characteristics of the implant material. The implant materials may be divided into bioactive, bioinert, and degradable/absorbable materials, depending on the reaction of the biosystem.

Implant materials include polymers, metallic materials, and ceramic materials (as a coating, for example). Biocompatible metals and metal alloys for permanent implants contain, for example, stainless steels (316L, for example), cobalt-based alloys (CoCrMo cast alloys, CoCrMo forged alloys, CoCrWNi forged alloys, and CoCrNiMo forged alloys, for example), pure titanium and titanium alloys (CP titanium, TiAl6V4, or TiAl6Nb7, for example), and gold alloys. For biocorrodible stents, the use of magnesium or pure iron, is known.

It is also known that a higher degree of biocompatibility may be achieved when implant materials are provided with coatings of materials which are compatible with tissue in particular. These materials are usually of an organic or synthetic polymeric nature, and sometimes are of natural origin.

The use of biocorrodible magnesium alloys for temporary implants having filigreed structures is made difficult in particular due to the fact that the implant degrades very rapidly in vivo. Various approaches have been discussed for reducing the corrosion rate, i.e., the speed of degradation. On the one hand, attempts have been made to retard the degradation with respect to the implant by development of appropriate alloys. On the other hand, coatings may be designed to temporarily inhibit the degradation. The latter approach thus requires that the coating prevent or inhibit the corrosion for a reproducible period of time, but after that time quickly allows complete disintegration of the implant.

SUMMARY

One or more of the previously described as well as other disadvantages of the prior art are eliminated or at least diminished by using an implant embodiment according to the invention having a base body composed of a biocorrodible magnesium alloy and a polylactide coating. This embodiment of the implant is characterized in that the coating contains seed crystals and/or lipophilic substances as additives.

DETAILED DESCRIPTION

At least some invention embodiments are based on the discovery that the corrosion of implants composed of biocorrodible magnesium alloys may be delayed in time by applying a polylactide-based coating which is characterized in that either the polymer is present in a finely-dispersed, crystalline state, and/or the coating contains hydrophobic additives. As a result of these measures the coating becomes more impermeable to the corrosion medium, resists corrosion for longer periods of time than the prior art, and thereby significantly lengthens service life of the implant. Poly-L-lactide or poly-D-lactide are two examples of suitable polyactides.

Seed crystals are added to the coatings of some embodiments to influence the crystallinity of the polymer. The morphology of the polymeric material is thus influenced in such a way that numerous very small crystalline domains form which are homogeneously distributed over the polymeric material. Microparticles based in particular on ash, graphite, clay minerals, or silicates (in particular kaolin) on which the crystal formation of the polymer is initiated are some examples of those that can be introduced as seed crystals, although others may be used in invention embodiments. Due to the fine distribution of these seed crystals superfine crystalline domains which are also homogeneously distributed over the polymer are produced. The crystalline fraction in the polymer may thus be increased compared to conventionally applied polymer layers, which in turn results in higher density of the material and reduced water uptake and less swelling. These are important benefits that solve or at least significantly mitigate the effects of many of the heretofore unresolved problems of the prior art, including but not limited to rate of degradation. The lower water content in crystalline polymers is responsible for the higher stability as the result of reduced hydrolytic degradation. In at least some embodiments, the proportion of amorphous/crystalline domains is independent of the material, and is determined by parameters such as type of polymer, symmetry, polymerization rate, and polydispersity; i.e., for a given material the crystalline fraction is specified when the material is in a thermodynamically stable state.

In the prior art, the ability of the material to form crystalline regions is reduced in particular when the polymer matrix is loaded with active substance. This may be counteracted by producing a particularly compact, less swelling polylactide layer having a high crystalline fraction. The seed crystals may be added in a quantity of 0.01-2% by weight, 0.2-1% by weight, or in other ranges relative to the total weight of the polymer. 0.2-1% by weight is believed to provide particular utility in many invention embodiments. A second example embodiment involves adding a lipophilic substance to the polymer, thereby increasing the overall hydrophobicity of the polymeric material. Water uptake by the polymer and swelling may thus be prevented. Squalene, squalane, or cholesterol are particularly suitable for this purpose, although other materials may be used. The lipophilic substances may be present in a quantity of 0.5-10% by weight, in particular 1-4% by weight, relative to the total weight of the polymer.

The lipophilic substances may have a log P value of >−0.5. The P value or also the octanol/water distribution coefficient is a dimensionless distribution coefficient which indicates the ratio of the concentrations of a chemical in a two-phase system composed of 1-octanol and water (at 25° C.). P is generally expressed in the form of the decadic logarithm as log P.

A coating within the meaning of the invention is an application of the components of the coating, at least in places, to the base body of the implant. The entire surface of the base body of the implant is covered by the coating in some embodiments. An example layer thickness is in the range of 1 nm to 100 µm, 300 nm to 15 µm, or in other ranges. The coating according to the invention may be applied directly to the implant surface, or additional intermediate layers may be provided; thus, the base body of the implant may optionally have an inorganic base layer which improves the adhesion of the coating according to the invention. One or more further layers (so-called topcoat layers, for example) may be applied to the coating according to the invention. These one or more layers may have compositions and thicknesses as may be desirable for particular applications. Methods for coating implants are known to one skilled in the art.

The term "biocorrodible" within the meaning of the invention refers to alloys in which degradation/conversion takes place in the physiological environment, so that the portion of the implant which is composed of the material is completely or at least predominantly no longer present.

In the present context, "magnesium alloy" is intended to be broadly interpreted as meaning a metallic structure whose primary component is magnesium. The primary component is the alloy component having the highest proportion by weight in the alloy. A proportion of the primary component may be greater than 50% by weight, or greater than 70% by weight. The composition of the alloy is to be selected so that the alloy is biocorrodible. Artificial plasma as specified under EN ISO 10993-15:2000 for biocorrosion testing (composition: NaCl 6.8 g/L, $CaCl_2$ 0.2 g/L, KCl 0.4 g/L, $MgSO_4$ 0.1 g/L, $NaHCO_3$ 2.2 g/L, $Na_2HPO_4$ 0.126 g/L, $NaH_2PO_4$ 0.026 g/L) is used as test medium for testing the corrosion characteristics of a particular alloy. For this purpose, a sample of the alloy to be tested is kept at 37° C. and pH 7.38 in a sealed sample container containing a defined quantity of the test medium. The samples are withdrawn at time intervals of a few hours to several months, depending on the anticipated corrosion characteristics, and analyzed in a known manner for signs of corrosion. The artificial plasma according to EN ISO 10993-15:2000 corresponds to a medium that is similar to blood, thus providing an opportunity to reproducibly duplicate a physiological environment within the meaning of the invention.

One particularly suitable alloy based on a magnesium alloy has the following composition: >90% magnesium, 3.7%-5.5% yttrium, 1.5%-4.4% rare earths (excluding yttrium), and the remainder <1%, wherein percentages refer to percent by weight. The formulation preferably also includes a magnesium alloy containing 3.7-5.5% by weight yttrium, 1.8-2.7% by weight neodymium, and 0.2-1.2% by weight zirconium. The formulation particularly preferably corresponds to the commercially available magnesium alloy WE43. The above-referenced materials and stated compositions are characterized by good processability and favorable release characteristics for magnesium for in vivo degradation of the carrier. One study, among others, is known from the literature concerning the degradation characteristics of a magnesium alloy under physiological conditions, which provides information concerning the particular factors and measures which are important for optimizing the release of active substance (Levesque, J., Dube, D., Fiset M. and Mantovani, D. (2003) Material Science Forum Vols. 426-432, pp. 225-238).

The term "corrosion" herein refers to the reaction of a metallic material with its environment whereby, when the material is used in a component, a measurable change in the material results in impairment of the function of the component. In the present context a corrosion system is composed of the corroding metallic material and a liquid corrosion medium whose composition reproduces the conditions in the physiological environment, or which is a physiological medium, in particular blood. Material factors which influence the corrosion include the composition and pretreatment of the alloy, microscopic and submicroscopic inhomogeneities, boundary zone characteristics, temperature and stress state, and in particular the composition of a layer covering the surface. With regard to the medium, the corrosion process is influenced by conductivity, temperature, temperature gradients, acidity, volume-to-surface ratio, concentration difference, and flow velocity.

Redox reactions occur at the phase boundary surface between material and medium. For a protective or inhibiting effect, protective layers which are present and/or the products of the redox reactions must form a structure with adequate resistance to the corrosion medium, have increased thermodynamic stability with respect to the surroundings, and be sparingly soluble or insoluble in the corrosion medium. Adsorption and desorption processes occur in the phase boundary surface, or more precisely, in a double layer which forms in this region. The processes in the double layer are characterized by the transport and diffusion processes which occur at that location. A gradual alkalization of the double layer is generally observed for magnesium alloys. Foreign matter deposits, impurities, and corrosion products influence the corrosion process. The processes during the corrosion, in particular the rate-determining step, are therefore very complex, and due to the lack of comparative data are difficult to predict, if at all, in particular with regard to a physiological corrosion medium, i.e., blood or artificial plasma. For this very reason (and others), the discovery of a corrosion-inhibiting coating, i.e., a coating which is used only for temporarily reducing the corrosion rate of a metallic material of the above-referenced composition in the physiological environment according to invention embodiments, is a measure outside the normal sphere of operations of one skilled in the art. This is particularly true for stents, which are subjected to localized high plastic deformation during the implantation. Conventional approaches using rigid corrosion-inhibiting layers are unsuitable under such demands. For these and other reasons, embodiments of the invention provide important benefits and advantages over the prior art.

Coatings of the invention as described herein achieve other advantages in that they remain highly flexible and subject to plastic deformation despite their high degree of corrosion resistance. This allows for such coatings to deform together with an underlying implant during implantation and avoid cracking, shifting or other coating failure that would otherwise expose the underlying implant to the environment.

The corrosion process may be quantified by expression as a corrosion rate. Rapid degradation is associated with a high corrosion rate, and vice versa. A coated implant within the meaning of the invention results in a decreased corrosion rate with regard to the degradation of the entire molded body. The corrosion-inhibiting coating according to the present invention may itself be degraded over time, or is able to provide increasingly less protection to the regions of the implant covered by the coating. Therefore, the progression of the corrosion rate for the overall implant is not linear. Instead, the corrosion rate is relatively low at the beginning of the developing corrosive processes (as the corrosion resistant coating corrodes slowly) and increases over time (after the coating has corroded to expose the implant which is more susceptible to corrosion). In at least some invention embodiments, the coating has an in-vivo corrosion rate that no more than half that of the implant (that is, the coating corrodes no more than twice as slow as the implant). This behavior is understood as temporary reduction of the corrosion rate within the meaning of the invention, and characterizes the corrosion-inhibiting coating. For many coronary stents, the mechanical integrity of the structure should be maintained over a period of three to six months after implantation.

"Implants" within the meaning of the invention are devices which are inserted into the body by surgical methods, and include attachment elements for bones, for example screws, plates, or pins, surgical suture material, intestinal clamps, vessel clips, prostheses for hard and soft tissue, and anchoring elements for electrodes, in particular for pacemakers or defibrillators. The implant is composed, completely or in part, of the biocorrodible material. When the implant is composed of the biocorrodible material only in part, this part must be appropriately coated. In many invention embodiments, the implant is a stent.

The polymer matrix may contain one or more active substances, which are released after the implantation. The active substance may be embedded in the polymeric material. Alternatively or additionally, the coating may contain particles which are composed of polylactide and an active substance, but which contain no additives. Due to the active substance loading and the lack of seed crystals or lipophilic substances as additives, the morphology of the polymeric material in these particles is less crystalline or hydrophobic compared to the coating according to the invention. However, these particles containing active substance are situated only on the surface of the coating, and therefore have little influence on the water uptake and swelling characteristics of the overall coating.

According to another example embodiment, the coating contains particles which are composed of polylactide and an additive (seed crystals or lipophilic substance), but which contain no active substances.

In some embodiments, layers containing active substance may be additionally applied to the exterior of the implant, which has already been treated with a corrosion-retarding layer composed of polymer matrix and additives; i.e., one or more layers containing active substance are additionally applied to the polylactide coating and/or to the implant base body. The additional layers containing active substance may either completely and or partially cover the implant surface—for a stent, preferably abluminally.

Within the meaning of the invention, an "active substance" is understood to mean a drug having pharmaceutical activity which is used in the human or animal body for the cure, mitigation, prevention, or detection of diseases. Active substances include in particular paclitaxel, sirolimus/rapamycin, and their derivatives, and prodrugs. Active substances which act on mTOR are particularly advantageous, as well as RAS inhibitors, in particular those which prevent RAS adhesion. Anti-inflammatory and antithrombogenic active substances are also advantageous.

Coatings of the invention advantageously can significantly increase support time of implants as compared to the same implant provided without a coating. For example, some implants of the invention, including stents, achieve support time that is increased by 2 weeks to 6 months or more in vivo, compared to an uncoated implant, as a result of the polylactide coating embodiments as described above.

Some example embodiments of the invention are explained in greater detail below with reference to exemplary embodiments.

Exemplary Embodiment 1

2 g poly-L-lactide (PLLA), 350 mg rapamycin, and 40 mg squalene were dissolved in approximately 1 L $CHCl_3$. The solution was applied, using a customary spray process, to a stent composed of a biocorrodible magnesium alloy.

Exemplary Embodiment 2

2 g poly-L-lactide (PLLA), 350 mg rapamycin, and 10 mg kaolin (finely ground; <0.5 µm) were dispersed in approximately 1 L $CHCl_3$. The suspension was applied, using a spray process, to a stent composed of a biocorrodible magnesium alloy.

Exemplary Embodiment 3

A first coating was provided according to exemplary embodiment 1 or 2, but without the addition of rapamycin.

The coated stent obtained was sprayed with a further coating solution containing PLLA and rapamycin in a 1:1 weight ratio in CHCl₃, at a distance of 30 cm on a PTFE plate at 50° C. The temperature and distance resulted in spray drying; the particles obtained were introduced/applied to the still-moist first coating. A further cover layer may optionally be applied.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implant having a base body comprised of a biocorrodible magnesium alloy and a corrosion-inhibiting polylactide coating, and wherein the corrosion-inhibiting polylactide coating contains a polylactide polymer and a compound selected from lipophilic substances, wherein the lipophilic substance is selected from the group consisting of squalene and squalane,
   wherein the compound is distributed homogeneously in the corrosion-inhibiting polylactide coating, and
   wherein the corrosion-inhibiting polylactide coating is applied directly over the biocorrodible magnesium alloy base body; and
   wherein the corrosion-inhibiting polylactide coating results in the implant having a non-linear corrosion rate and a support time that is increased by at least 2 weeks after the implantation as compared to an uncoated implant having a base body comprised of a biocorrodible magnesium alloy.

2. An implant according to claim 1, wherein the polylactide polymer is formed from poly-L-lactide.

3. An implant according to claim 1, wherein the polylactide is formed from poly-D-lactide.

4. An implant according to claim 1, wherein the corrosion-inhibiting polylactide coating contains the lipophilic substances and seed crystals, and wherein the lipophilic substances have a log P value of greater than −0.5.

5. An implant according to claim 4, wherein the corrosion-inhibiting polylactide coating contains the seed crystals selected from the group comprising ash, graphite, silicates, and clay minerals.

6. An implant according to claim 4, wherein the corrosion-inhibiting polylactide coating is crystalline and contains the seed crystals that have a weight fraction of 0.01-2%, relative to the total weight of the polylactide coating.

7. An implant according to claim 4, wherein the corrosion-inhibiting polylactide coating is a first coating that covers the entirety of the base body, and wherein:
   the polylactide polymer is poly-L-lactide;
   the first coating contains the seed crystals and the lipophilic substances including one or more of squalene or squalane in 1-4% by weight relative to the total weight of the polylactide coating, the lipophilic substances resulting in the first coating being hydrophobic;
   the first coating has a thickness of between 300 nm to 15 µm;
   the first coating results in a non-linear corrosion rate of the implant in-vivo wherein the first coating corrodes at a slower rate than the implant; and,
   a second coating is provided overlaying the first coating, the second coating including a drug having a pharmaceutical activity.

8. An implant according to claim 1, wherein the corrosion-inhibiting polylactide coating contains an active substance and has a thickness of between 300 nm to 15 µm.

9. An implant according to claim 1, wherein the implant is a stent, and wherein the biocorrodible magnesium alloy includes at least 90% (wt.) magnesium, 3.7-5.5% (wt.) yttrium, 1.8-2.7% (wt.) neodymium, and 0.2-1.2% (wt.) zirconium.

10. An implant according to claim 1, wherein the coating contains particles which are composed of polylactide and an active substance, but which do not contain any additives.

11. An implant according to claim 1, wherein the corrosion-inhibiting polylactide coating is hydrophobic and contains the lipophilic substances having a weight fraction of 0.5-10% by weight, relative to the total weight of the polylactide coating.

12. An implant according to claim 1, wherein one or more second layers containing active substances are additionally applied to the corrosion-inhibiting polylactide coating.

13. An implant according to claim 1, wherein the implant has a support time which is increased by 2 weeks to 6 months in vivo as compared to the same implant without a coating, and has a non-linear corrosion rate.

14. A stent for use in a mammal to support a vessel, hollow organ, or duct system, the stent comprising:
   a base body comprised of a biocorrodible magnesium alloy containing at least yttrium and at least 90% (wt) magnesium;
   a corrosion-inhibiting coating covering the base body and wherein the corrosion-inhibiting coating is applied directly over the base body, the corrosion-inhibiting coating having an in-vivo corrosion rate that is no more than half that of the underlying base body, the corrosion-inhibiting coating including one or more of poly-D-lactide and poly-L-lactide, and containing a compound selected from the group consisting of lipophilic substances selected from the group consisting of squalene and squalane in a concentration of between 0.5-10% (wt), and wherein the corrosion-inhibiting coating has a thickness of between 300 nm to 15 µm; and,
   wherein the corrosion-inhibiting coating results in the stent having non-linear corrosion rate and a support time that is increased by at least 2 weeks in vivo as compared to an uncoated stent with a base body comprised of a biocorrodible magnesium alloy containing at least yttrium and at least 90% (wt) magnesium.

15. A stent as in claim 14 wherein:
   the base body alloy further contains neodymium and zirconium; and,
   the coating contains the lipophilic substances and does not contain any seed crystals, the lipophilic substances provided in a concentration of 1-4% (wt), the presence of the lipophilic substances resulting in the coating being highly hydrophobic, and the coating has a thickness of between about 300 nm to 15 µm; and
   wherein the coating further includes a drug having pharmaceutical activity.

16. A stent as in claim 14 wherein the corrosion-inhibiting coating is a first coating, and further including a second coating overlaying the first coating, the second coating containing an active substance selected from the group consisting of paclitaxel, and sirolimus/rapamycin and their derivatives.

17. The stent of claim 14, wherein the corrosion-inhibiting coating further contains seed crystals, and wherein the seed crystals and the lipophilic substances are distributed homogeneously in the corrosion-inhibiting coating.

18. An implant having a base body comprised of a biocorrodible magnesium alloy and a corrosion-inhibiting polylactide coating containing a polylactide polymer, seed crystals and a lipophilic substance selected from squalene and squalane, wherein the seed crystals and the lipophilic substance are distributed homogeneously in the corrosion-inhibiting polylactide coating, and wherein the corrosion-inhibiting polylactide coating is applied directly over the biocorrodible magnesium alloy base body; and wherein the corrosion-inhibiting polylactide coating results in the implant having a non-linear corrosion rate and a support time that is increased by at least 2 weeks after the implantation as compared to an uncoated implant having a base body comprised of a biocorrodible magnesium alloy.

\* \* \* \* \*